(12) United States Patent
San Juan

(10) Patent No.: US 9,662,556 B2
(45) Date of Patent: May 30, 2017

(54) ELECTRONIC SPORTS TRACKING AND COACHING SYSTEM

(71) Applicant: Nicolas San Juan, American Fork, UT (US)

(72) Inventor: Nicolas San Juan, American Fork, UT (US)

( * ) Notice: Subject to any disclaimer, the term of this patent is extended or adjusted under 35 U.S.C. 154(b) by 0 days.

(21) Appl. No.: 14/253,973

(22) Filed: Apr. 16, 2014

(65) Prior Publication Data

US 2014/0309058 A1    Oct. 16, 2014

Related U.S. Application Data

(60) Provisional application No. 61/812,567, filed on Apr. 16, 2013.

(51) Int. Cl.
*A63B 69/00* (2006.01)
*A63B 43/00* (2006.01)
*A63B 71/06* (2006.01)
*A63B 24/00* (2006.01)

(52) U.S. Cl.
CPC .......... *A63B 69/00* (2013.01); *A63B 24/0075* (2013.01); *A63B 43/00* (2013.01); *A63B 69/002* (2013.01); *A63B 71/0622* (2013.01); *A63B 2071/063* (2013.01); *A63B 2071/0625* (2013.01); *A63B 2071/0661* (2013.01); *A63B 2208/12* (2013.01); *A63B 2220/10* (2013.01); *A63B 2220/13* (2013.01); *A63B 2220/16* (2013.01); *A63B 2220/20* (2013.01); *A63B 2220/35* (2013.01); *A63B 2220/53* (2013.01); *A63B 2220/803* (2013.01); *A63B 2220/833* (2013.01); *A63B 2225/50* (2013.01)

(58) Field of Classification Search
None
See application file for complete search history.

(56) References Cited

U.S. PATENT DOCUMENTS

| 4,595,200 | A | | 6/1986 | Shishido | |
|---|---|---|---|---|---|
| 5,288,069 | A | * | 2/1994 | Matsumoto | 473/570 |
| 5,375,839 | A | | 12/1994 | Pagani | |
| 5,445,375 | A | * | 8/1995 | Sweeny | A63B 43/00 273/146 |
| 5,810,685 | A | | 9/1998 | Willner et al. | |
| 6,582,330 | B1 | * | 6/2003 | Rehkemper et al. | 473/570 |

(Continued)

*Primary Examiner* — Tramar Harper
(74) *Attorney, Agent, or Firm* — Global Intellectual Property Agency, LLC; Daniel Boudwin

(57) ABSTRACT

An electronic tracking and coaching system adapted for use in training for various sports is provided. The present invention includes a sports ball that contains a plurality of sensors, a wireless transceiver, a storage medium adapted to store voice commands or noises to be played upon the occurrence of a pre-determined event, and a speaker. The ball's sensors are adapted to monitor the movement of the ball, the level and direction of force applied to the ball, and other such variables relevant to playing a sport with a ball. The device further includes a monitoring apparatus that is worn by the user and tracks all of his or her movement and stores that movement data for later access. The voice commands of the ball provide coaching direction to the user and the user can upload the stored data to data visualization software to precisely monitor his or her actions.

20 Claims, 6 Drawing Sheets

(56) References Cited

U.S. PATENT DOCUMENTS

| | | | |
|---|---|---|---|
| 7,163,489 B1* | 1/2007 | Nelson | A63B 71/0622 |
| | | | 482/1 |
| 8,289,185 B2 | 10/2012 | Alonso | |
| 8,951,151 B2* | 2/2015 | Glowinski | 473/570 |
| 2003/0109339 A1* | 6/2003 | Oister et al. | 473/570 |
| 2004/0213087 A1* | 10/2004 | Gillette | G04F 8/08 |
| | | | 368/107 |
| 2005/0051961 A1* | 3/2005 | Hodgeman | A63F 7/06 |
| | | | 273/288 |
| 2007/0178967 A1* | 8/2007 | Rosenberg | 463/39 |
| 2007/0213989 A1* | 9/2007 | Cooksy | G06Q 10/06 |
| | | | 704/275 |
| 2008/0015064 A1* | 1/2008 | Nelson et al. | 473/571 |
| 2009/0048039 A1* | 2/2009 | Holthouse et al. | 473/415 |
| 2009/0048044 A1 | 2/2009 | Oleson et al. | |
| 2010/0184563 A1* | 7/2010 | Molyneux et al. | 482/1 |
| 2011/0130230 A1* | 6/2011 | Solberg et al. | 473/570 |
| 2011/0237367 A1* | 9/2011 | Kodama et al. | 473/570 |
| 2012/0139727 A1* | 6/2012 | Houvener et al. | 340/540 |
| 2012/0244969 A1* | 9/2012 | Binder | 473/570 |
| 2012/0277040 A1 | 11/2012 | Vincent et al. | |
| 2012/0316011 A1* | 12/2012 | Milosevic | G09B 19/0038 |
| | | | 473/450 |

* cited by examiner

ELECTRONIC SPORTS TRACKING AND COACHING SYSTEM

CROSS REFERENCE TO RELATED APPLICATION

This application claims the benefit of U.S. Provisional Application No. 61/812,567 filed on Apr. 16, 2013 entitled "e-SportCoach." The above identified patent application is herein incorporated by reference in its entirety to provide continuity of disclosure.

BACKGROUND OF THE INVENTION

Field of the Invention

The present invention relates to sound-emitting balls and electronic sports training systems. More specifically, the present invention relates to an electronic sports training system that comprises an electronic ball and a user-worn monitoring device. The ball monitors and stores a variety of variables associated with the use of the ball, including its position, the force applied to the ball, the direction of the forces applied to the ball, the orientation of the ball, the spin of the ball, and other such variables. The user-worn monitoring device also stores variables associated with the movement of the user. These stored data sets can then be uploaded to a data visualization system and the data visualization system calculates and plots graphical representations of the user, the user's path, the ball, and the ball's path in order to provide a complete picture of the user's training. Furthermore, the ball is adapted to emit a plurality of sounds, comments, or commands to the user based upon the occurrence of certain events or the skill level of the user.

Training for a sport outside of directly-supervised coaching sessions can be a difficult and unproductive proposition for many individuals, especially if they are a novice to the sport or very young, since it is often difficult to know whether one is truly performing a task correctly without a knowledgeable third party observer being present. Improving at a sport can also be very difficult for intermediate-level individuals because said users tend to plateau without further direction from coaches and other individuals knowledge about the proper techniques to utilize when playing the sport. Furthermore, many young individuals have the desire to get into and play sports, but they lack the requisite level of encouragement to get them beyond the initial difficultly hump associated with learning the sport and developing positive health habits.

Electronic sports training systems and sound-emitting balls are currently known in the prior art. The electronic training systems generally comprise a plurality of sensors to be worn by the individual, a means for recording and storing the data captured by the sensors, and a means for translating the discrete data measurements into meaningful results that may be utilized by the user to improve or track his or her performance. These training systems lack any direct, immediate feedback provided to the user in the form of sounds or comments. Therefore, the user is unable to alter his performance and improve his or her skills while in the act of playing the sport and instead must rely on the ability to analyze the data, interpret the data into meaningful results, and then apply the conclusions garnered from the interpreted data at a later training time. This is an inefficient system because users therefore spend entire training sessions practicing improperly without any direction as to such from the system and they are forced to perfectly analyze and alter their playing or practicing style without any direct input from a third-party observer. Sound-emitting sports balls are also known in the prior art, however they lack any means for tracking and monitoring the movement of the ball, the force applied to the ball, or the orientation or spin of the ball and lack the ability to dynamically provide comments to the user regarding his or her performance based upon these tracked variables. Therefore, there is a need in the prior art for a sports training and coaching system that continuously tracks variables associated with both the user and the ball and is adapted to dynamically provide feedback to the user based upon these variables.

An electronic sports training and coaching system is provided to simulate real-time coaching for any player of any skill level. The system comprises a ball having an electronic monitoring system, a user-worn apparatus for monitoring the actions of the user, and a visual representation system to which the data from the aforementioned components can be uploaded. The ball further comprises a plurality of sensors, a speaker for emitting sounds, comments, or coaching commands, a storage medium for storing said sounds and the tracked data from the sensors, a wireless transceiver for uploading said data and downloading program updates, and a power supply. The visual representation system is software on a secondary electronic device to which the data tracked by the ball and user-worn apparatuses may be uploaded. Once uploaded to the visual representation system, the data is translated into visual representations of the ball and the user so that the user can track his or her progress around the field of play and preferably compare his movement to a desire movement route. The ball is configurable to emit comments in response to the occurrence of various events or coaching commands at random intervals to train the user to respond to direction from a third-party and to improve the user's response time and agility.

Description of the Prior Art

Devices have been disclosed in the prior art that relate to sound-emitting balls and electronic sports training and tracking systems. These include devices that have been patented and published in patent application publications. These devices generally relate to balls having speakers and monitoring systems comprising a plurality of sensors that are worn by the user, respectively. The following is a list of devices deemed most relevant to the present disclosure, which are herein described for the purposes of highlighting and differentiating the unique aspects of the present invention, and further highlighting the drawbacks existing in the prior art.

Some such devices include U.S. Pat. No. 4,595,200 to Shishido, U.S. Pat. No. 5,275,839 to Pagani, U.S. Pat. No. 5,810,685 to Willner et al., and U.S. Pat. No. 6,582,330 to Rehkemper et al., which all disclose various sports balls that are adapted to emit sounds in response to various stimuli or track certain statistics. All of these devices fail to provide a ball that is adapted to dynamically provide coaching commands to a user and is adapted to logically provide comments to the user based upon the user's performance, as detected by the ball's sensors.

Other such devices include U.S. Pat. No. 8,289,185 to Alonso and U.S. Published Patent Application Publication No. 2009/0048044 to Vincent et al., which disclose systems for monitoring the movement and performance of a user in the context of playing or training for a sport. These devices are also adapted to track data associated with a user's movement and actions, however, they lack a means for dynamically and immediately providing coaching cues or commands to an individual based upon the individual's current performance.

The present invention provides an electronic sports tracking and training system. The system comprises a ball that has a plurality of sensors for tracking its movement and the forces imparted upon the ball, a user-worn tracking system that also comprises a plurality of sensors for tracking movement, and a data visualization system to which the stored data may be uploaded and mapped in either a two-dimensional or a three-dimensional format so that it can be visualized by a user. These components work together to provide users with a total picture of their movement relative to the movement of the ball. The ball further comprises a plurality of sounds or comments that the device plays in response to certain variables being within pre-determined tolerance thresholds that are specifically assigned to each sound or comment. The ball will also play coaching commands that direct the user to take certain actions at random intervals. It substantially diverges in design elements from the prior art and consequently it is clear that there is a need in the art for an improvement to existing sports tracking and training devices. In this regard the instant invention substantially fulfills these needs.

SUMMARY OF THE INVENTION

In view of the foregoing disadvantages inherent in the known types of sports training and tracing devices now present in the prior art, the present invention provides a new sports tracking and coaching system wherein the same can be utilized for providing convenience for the user when training for a sport without third-party supervision.

It is therefore an object of the present invention to provide a new and improved sports tracking and coaching system that has all of the advantages of the prior art and none of the disadvantages.

It is another object of the present invention to provide a sports tracking and coaching system that comprises a plurality of sensors for monitoring the user's speed, distance travelled, orientation, and other such variables.

It is another object of the present invention to provide a sports tracking and coaching system that comprises a plurality of sensors for monitoring the sports ball's speed, distance travelled, orientation, force imparted on the ball, rate of rotation, and other such variables.

Another object of the present invention is to provide a sports tracking and coaching system that dynamically and instantly provides feedback to the user based upon his performance as measured by variables such as the force with which the user strikes the ball, the rate of rotation of the ball, the distance travelled by the ball in the air, and other such variables.

Yet another object of the present invention is to provide a sports tracking and coaching system that provides coaching commands to the user at random intervals in order to train the user to follow direction from a third-party or improve the user's response time and agility.

Yet another object of the present invention is to provide a sports tracking and coaching system that may comprise a variety of different sports balls, including soccer balls, footballs, basketballs, and such.

Still yet another object of the present invention is to provide a sports tracking and coaching system that has a means for visualizing and playing back the data tracked by the various components of the present invention.

Another object of the present invention is to provide a sports tracking and coaching system that may be readily fabricated from materials that permit relative economy and are commensurate with durability.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
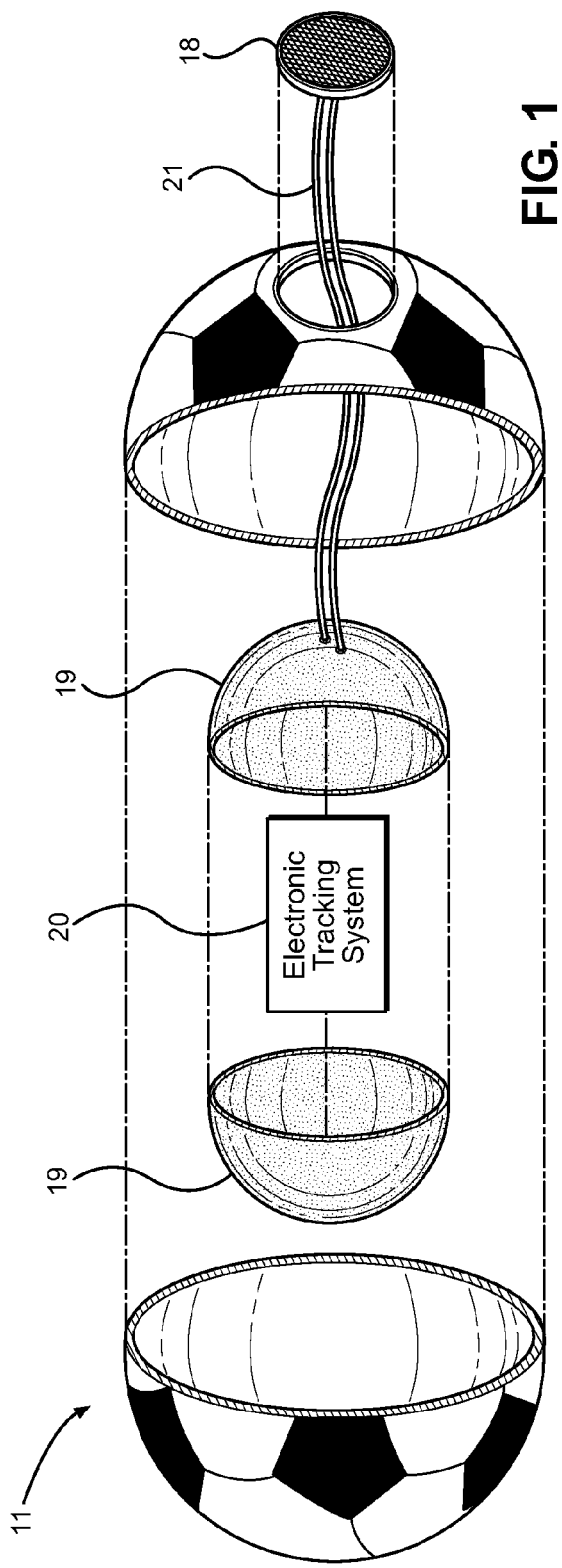
FIG. 1 shows an exploded view of the sports ball of the present invention.

Reference is made herein to the attached drawings. Like reference numerals are used throughout the drawings to depict like or similar elements of the electronic sports tracking and coaching system. For the purposes of presenting a brief and clear description of the present invention, the preferred embodiment will be discussed as used for tracking various variables related to playing a sport using a ball, including the force imparted upon the ball by the user, the degree of spin, the distance travelled by the ball, and so on, and storing the tracked variables so that they can be displayed at a later time on a secondary electronic device. The figures are intended for representative purposes only and should not be considered to be limiting in any respect.

Figure 2:
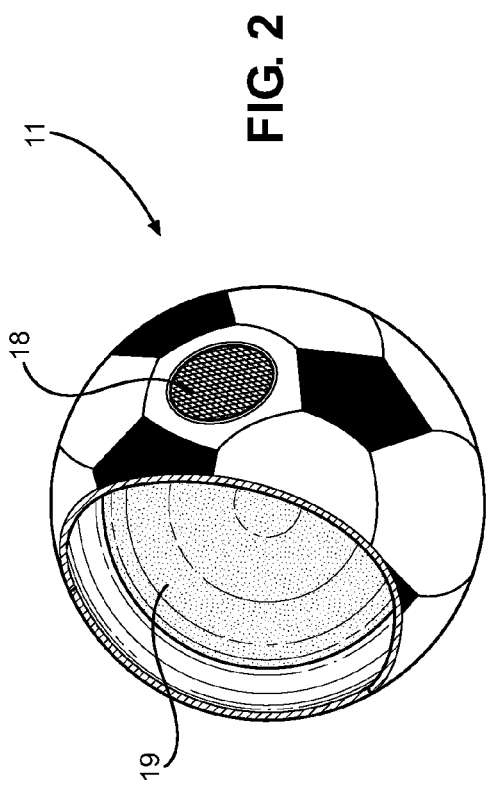
FIG. 2 shows a cutout view of the sports ball of the present invention.

Referring now to FIGS. 1 and 2, there are shown an exploded view and a cutout view of the sports ball component of the present invention. The present invention comprises an electronic tracking system that is specifically adapted for application in various sports. The present invention comprises a ball 11 having at least one speaker 18 disposed on its exterior layer 22 and an electronic system 20 held securely within a protective inner shell layer 19. The ball 11 may comprise any type of sports ball, including a soccer ball, a football, a basketball, and a rugby ball. The various sports balls 11 depicted in the provided figures are merely intended to be exemplary and should not be interpreted to be limited as to those specific embodiments or designs in any way. The ball 11 is composed of any material known in the prior art of sports balls. The ball 11 of the present invention is otherwise constructed in the ordinary fashion of that particular type of sports ball, except insofar as it has at least one speaker 18 disposed on its exterior surface and a protective inner shell 19 protecting the present invention's internal electronic system 20. The present ball 11 further comprises a power supply (not shown), which may be of any type commonly known in the prior art, including batteries that are disposed within a compartment having a removable lid or at least one solar cell. No claim is made as to the specific power supply utilized by the present invention.

The internal electronic system 20 comprises a plurality of sensors, a wireless transceiver, and a memory unit. The sensors preferably comprise at least one accelerometer, at least one gyroscope, and other such sensors used to detect the force imparted on the ball by an impact, the orientation and position of the ball, the distance travelled by the ball, and other such variables. The components of the electronic system 20 are held securely within the protective inner shell 19, which protects them from being damaged by impacts on the ball 11. The inner shell 19 may comprise a gel layer, a rigid plastic liner, or any other such material commonly known in the prior art to absorb and dissipate forces. The exact composition and configuration of the inner shell 19 varies based upon the type of ball 11 of the present invention.

In one embodiment of the present invention, at least one speaker 18 is disposed on the exterior surface of the ball 11 and is connected to the electronic system 20 via wiring 21. The speaker 18 is designed to emit noises, commands, comments, and other such sounds based upon various stimuli detected by the electronic system 20 of the present invention. The speaker 18 accesses these noises, commands, comments, and other such sounds from the electronic system's 20 memory unit, which are stored thereon. Whenever the electronic system 20 detects the occurrence of a discrete event, such as a user kicking the ball, the electronic system 20 characterizes the event and compares the parameters of the characterized event to a list of sounds stored within the memory unit. Each sound has a range of parameters that trigger it and if the characterized event falls within the parameters of the given sound, then the electronic system 20 triggers that sound such that it is emitted from the speaker 18. For example, if the user kicks the ball with 50 N of force, the accelerometer sensors of the electronic system 20 detect this force imparted on the ball 11, characterize the force exerted on the ball as 50 N, then compares the characterized variable to the list of sounds contained within the present invention's memory unit that are designed to trigger when a 50 N force is imparted on the ball. Preferably, the various sounds stored within the memory unit will be provided ranges of forces (or other variables) from which to respond, therefore a single discrete event may fall within the ranges of multiple stored sounds. In this case, the electronic system 20 organizes every sound that is triggered by the value of the discrete event's variable or variables, generates a sub-list of those triggered sounds, and then randomly chooses which sound to play from the generated sub-list. Some sounds may be triggered by multiple variables associated with a discrete detected event, such as force imparted on the ball and the spin of the ball. The present invention thereby provides a sports ball that is able to respond to various stimuli in a logical and consistent manner, providing entertainment and immediate, educational feedback to users to reinforce positive sports habits and allow said users to hone their skills.

Figure 3A:
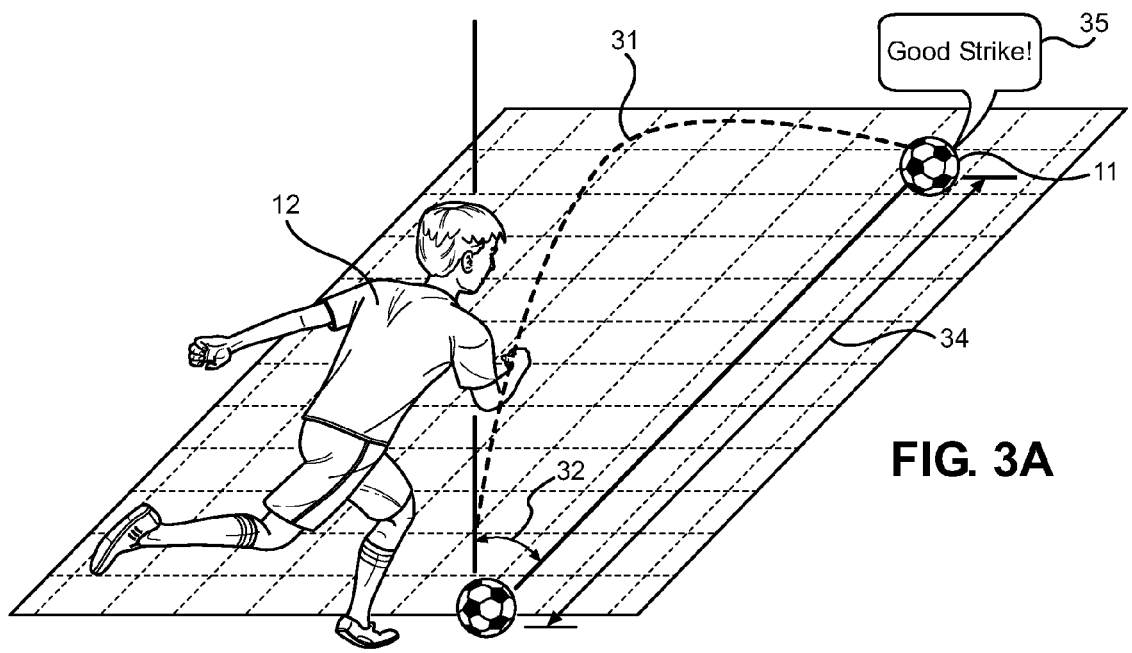
FIG. 3A shows an isometric view of the trajectory of the electronic ball of the present invention after being struck by a user.
Figure 3B:
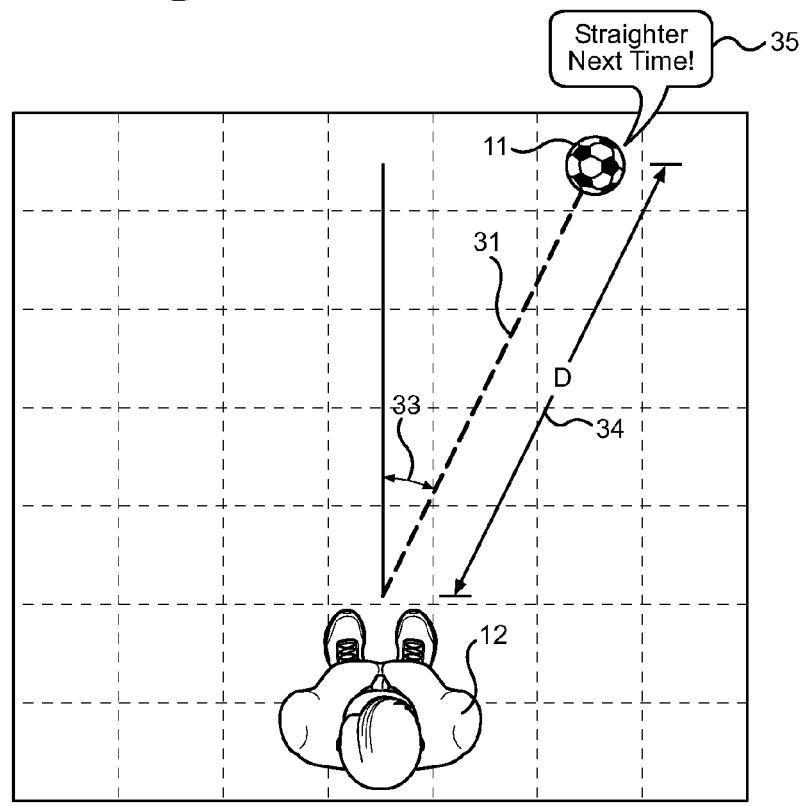
FIG. 3B shows a top-down view of the trajectory of the electronic ball of the present invention after being struck by a user.

Referring now to FIGS. 3A and 3B, there are shown various views of the trajectory of the electronic ball of the present invention after being struck by a user. The electronic system's sensors are able to detect a variety of variables associated with the use of sports ball 11. The sensors utilized by the internal electronic system of the present invention may comprise at least one accelerometer for measuring the amount and direction of force imparted on the ball 11, at least one gyroscope for measuring the orientation, spin, and launch angle of the ball 11, and a means for detecting the distance travelled by the ball 11. The various sensors work in combination to continually monitor and characterize the aforementioned tracked variables and store these tracked variables in the present invention's memory unit so that they can be accessed at a later time.

In the depicted embodiment of the present invention, the ball 11 comprises a soccer ball. However, the present invention does not comprise a single, specific type of sports ball and therefore no claim is made as such. The depicted embodiment of the present invention is intended to be exemplary only and not to be limited as to a single type of sports ball in any way. Furthermore, the variables tracked by the present invention are also exemplary only; no claim is made as to the specific types or configurations of sensors and therefore no claim is made as to the specific variables tracked by the present invention. In the contemplated embodiment of the present invention depicted in FIGS. 3A and 3B, the variables tracked by the present invention's sensors include the distance 34 travelled by the ball 11, the launch angle 32, the drift angle 33, the orientation, the spin, and the force imparted on the ball by the user at the point of impact and when the ball ultimately strikes the ground. These variables may be used in combination to track the trajectory 31 and the position of the ball 11. These variables are therefore able to monitor and track how hard the ball was struck by the user, how cleanly the ball was struck, how high the ball traveled, how far the ball travelled, and so on. The present invention is then able to choose a sound or comment 35 to play based upon the aforementioned variables, such as "Good strike!" as shown in FIG. 3A or "Straighter next time!" as shown in FIG. 3B. The comments 35 played by the present invention will be relevant to the event that occurred, e.g. the "Good strike!" comment 35 will be played when the user strikes the ball with a degree of force above a certain pre-determined threshold.

In alternative embodiments of the present invention wherein the ball 11 is other types of sports balls, such as football or basketballs, the present invention may comprise other sensors and be configured to track other variables than in the depicted embodiment of the present invention wherein the ball 11 is a soccer ball. For example, in an embodiment of the present invention wherein the ball 11 is a football, the present invention may preferentially track the spin of the ball when in the air in order to determine whether a tight spiral was thrown, which is generally indicated by a high rate of rotation by the ball 11, or a poor spiral was thrown, which is generally indicated by a law rate of rotation by the ball 11. The present invention may then make an appropriate comment 35 based upon the tracked rate of rotation of the ball 11. The same concept can then be applied to a variety of different types of sports balls 11 and a variety of variables tracked by the sensors.

Figure 4:
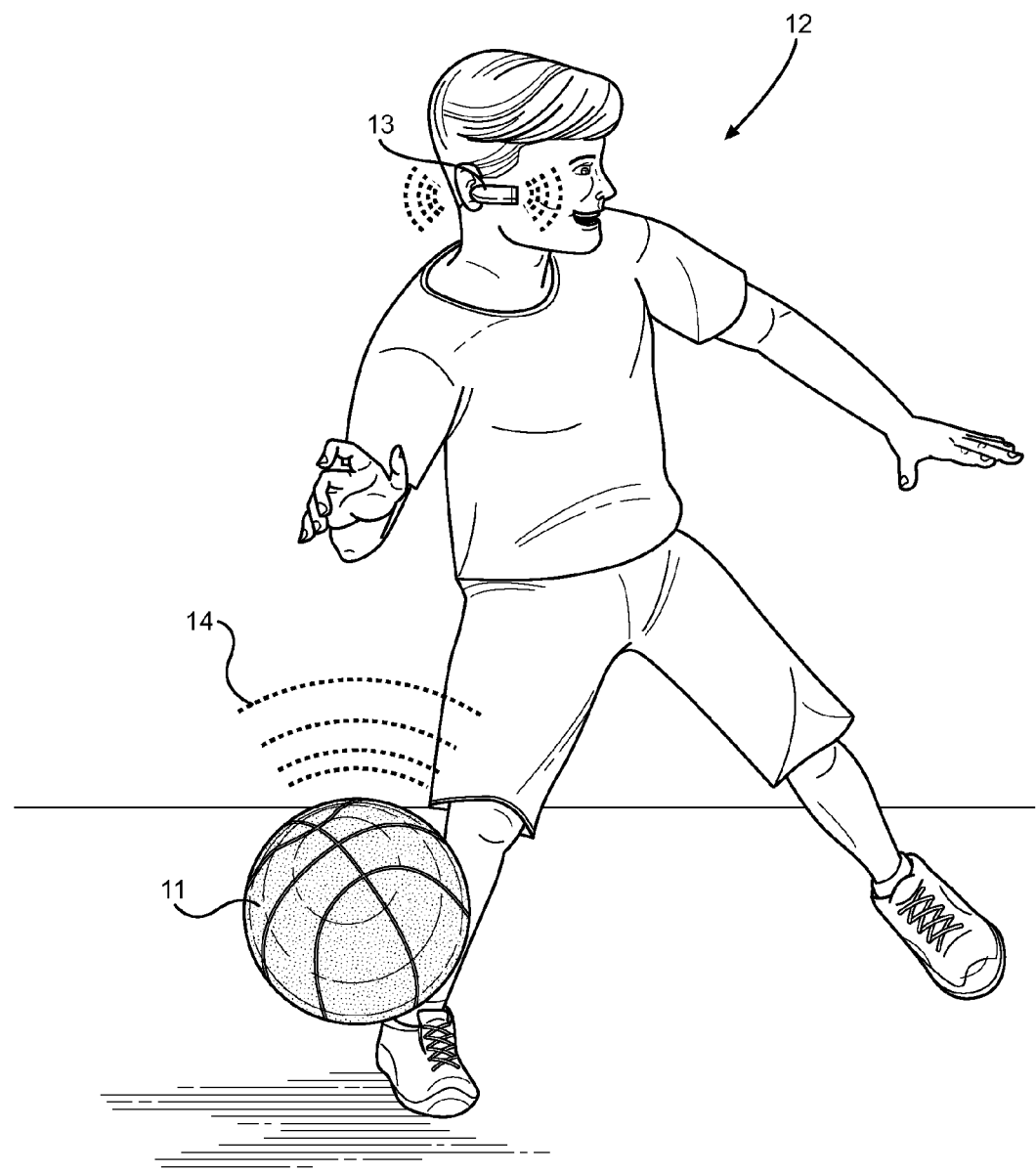
FIG. 4 shows a perspective view of an alternative embodiment of the present invention having a headset in use by an individual.

Referring now to FIG. 4, there is shown a perspective view of an alternative embodiment of the present invention having a headset in use by an individual. In an alternative embodiment of the present invention, the ball 11 lacks a speaker and instead wirelessly transmits 14 the comments or other sounds to a wireless headset 13, headphone, earphone, mobile electronic device, or other such device. This alternative embodiment of the present invention otherwise acts and functions exactly the same as the embodiment of the present invention herein described. The wireless connection 14 between the headset 13 and the ball 11 comprises any type of wireless connection, such as a Bluetooth connection. In an alternative embodiment of the present invention, the ball 11 is instead wirelessly connected to a mobile electronic device, such as a smartphone, to which a wireless headset 13 may in turn be connected. In a further alternative embodiment of the present invention, the ball 11 contains both a speaker and a means for wirelessly transmitting comments and other sounds to a headset 13. In this embodiment, when there is no headset 13 connected with the device, the present invention defaults to emitting the triggered sounds through the speaker. When there is a headset 13 connected with the device, then the present invention automatically transmits the sounds or comments to the headset 13 in the same manner as described above.

Figure 5:
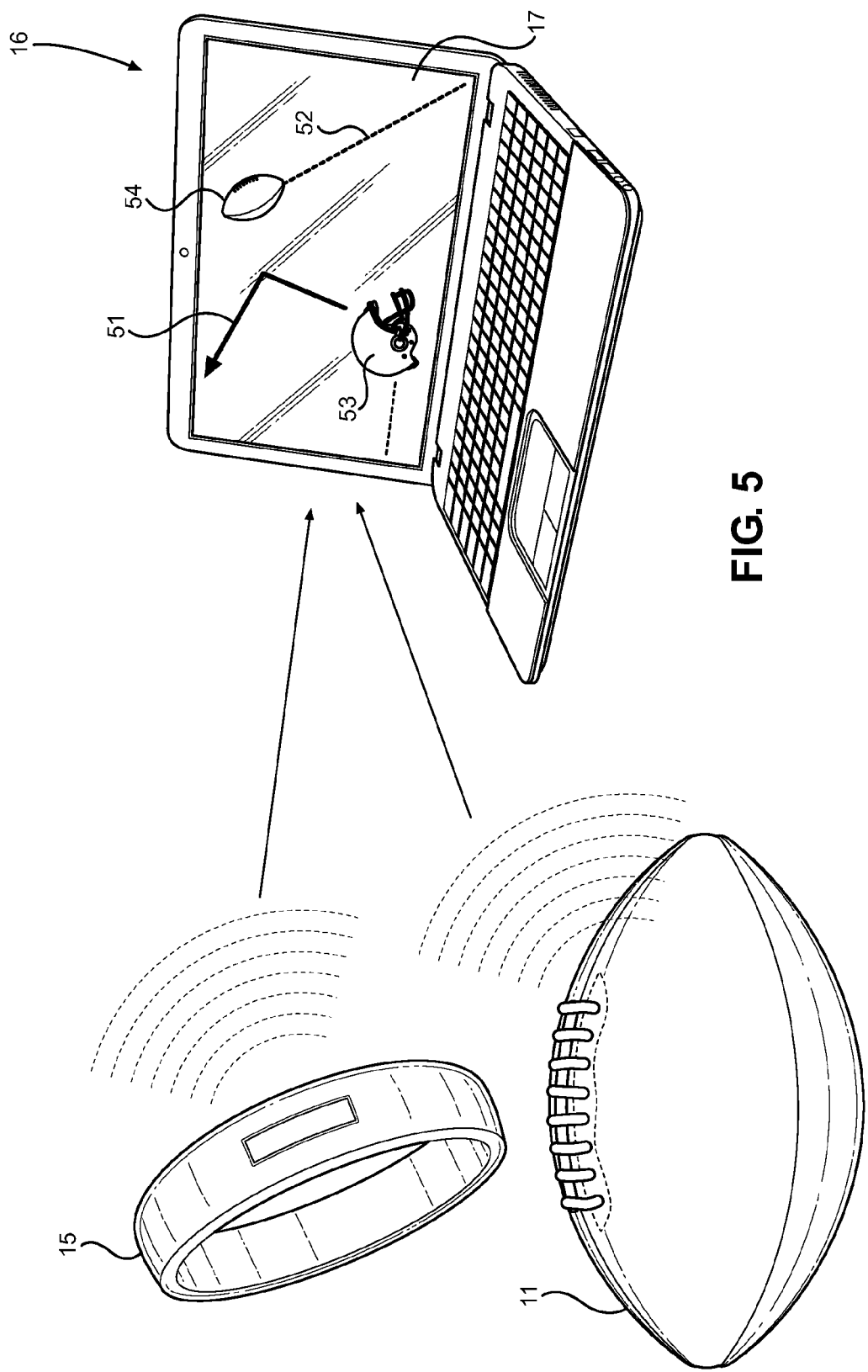
FIG. 5 shows a diagram illustrating the electronic ball and the wristband components of the present invention uploading tracked data to an electronic processing device.
Figure 6:
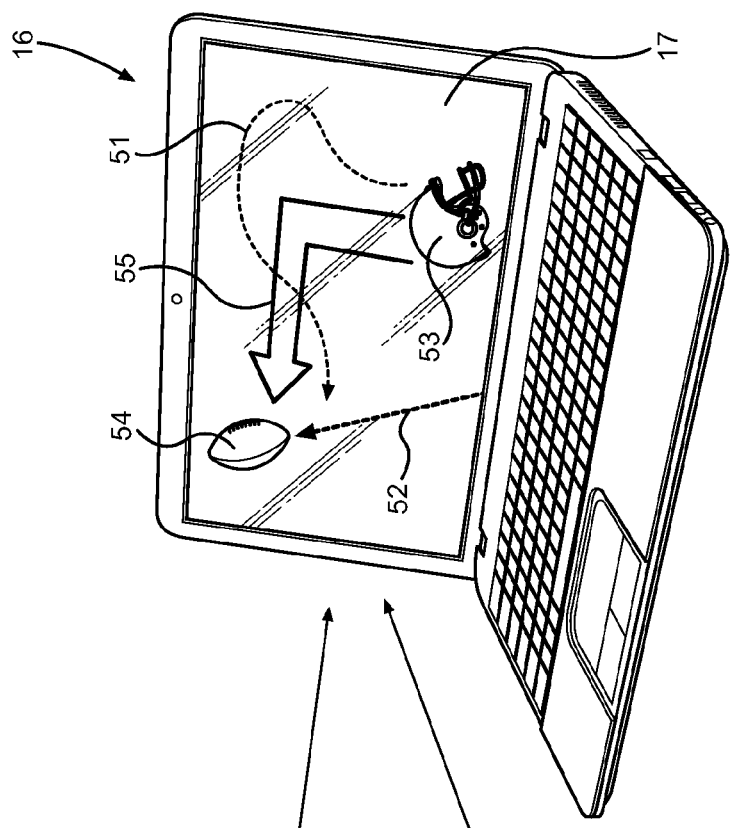
FIG. 6 shows a diagram illustrating uploaded data tracked by the electronic ball and wristband components of the present invention being compared to a visual representation of the desired route for the user to take.
Figure 6:
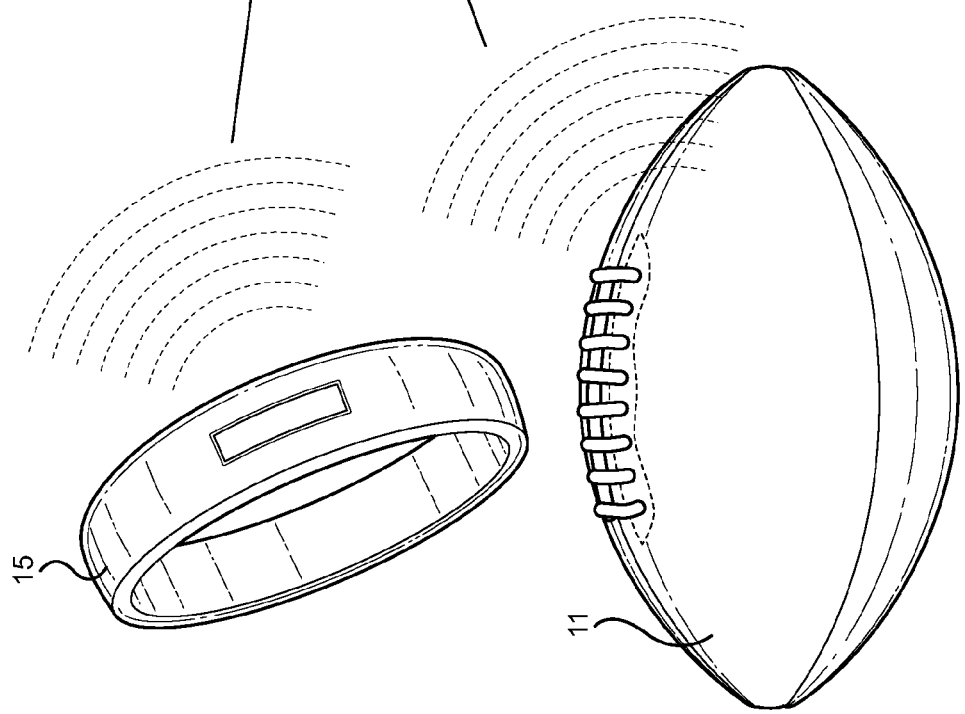

Referring now to FIGS. 5 and 6, there are shown diagrams illustrating the electronic ball and the wristband components of the present invention uploading data to a secondary electronic device. In addition to the electronic ball 11, the present invention may further comprises a user electronic tracking apparatus 15 that is adapted to be worn by the user. In the depicted embodiment of the present invention, the user electronic tracking apparatus 15 is a wristband. In other embodiments of the present invention, the user electronic tracking apparatus 15 may comprise a waistband, an anklet, or any other device that is capable of being worn by a user and housing a plurality of sensors for tracking movement and forces generated by the user when in use. The user electronic tracking apparatus 15, like the ball 11, comprises a plurality of sensors, such as accelerometers and gyroscopes, a memory unit, and a wireless transceiver. The user electronic tracking apparatus 15 functions similarly to the ball 11 in that the data characterized and collected by the device is stored in a memory unit for retrieval at a later time. The user electronic tracking apparatus 15 may track the average speed of the user, the user's acceleration over various intervals, the total distance travelled by the user, and other such variables. These tracked variables, when viewed in combination with the data garnered by the ball 11 component of the present invention, provide a total picture as to the actions by the user when playing or practicing with the ball 11. The user electronic tracking apparatus 15 lacks a speaker or a means for wirelessly sending sounds or comments to a user, unlike the ball 11 of the present invention.

In one embodiment of the present invention, the data tracking system is designed such that it takes one measurement from each of its sensors at a pre-determined time interval, thereby generating a database of time-indexed measurements corresponding to each of its sensors. When connected to the data visualization system, all of this data is uploaded thereto, characterized, and then translated into a visual representation of the movement of both the ball 54 and the user 53. The visual representation system is able to calculate the position of both the ball and the user by comparing the indexed data measurements at a given interval to the indexed data measurements at the prior time interval. The difference in speed and orientation at each of the given time intervals allows the visual representation system to successively calculate and plot the changing position of both the user and the ball and generate visual representations 53, 54 of them on the display 17.

The electronic ball 11 and user electronic tracking apparatus 15 components of the present invention can be wirelessly connected to a secondary electronic device 16 via any means known in the prior art, including a Bluetooth connection, a WiFi connection, and such. Once connected to the secondary electronic device 16, the data stored on the tracking devices 11, 15 can be wirelessly uploaded thereto. Once uploaded to the secondary electronic device 16, the data is then uploaded to software that generates visual representations of the stored data that are shown on a display screen 17. The visual representation of the data tracked by the tracking devices 11, 15 preferably comprises a representation of the player's actual path 51, the trajectory 52 of the ball, a player icon 53, and a ball icon 54. The player icon 53 can comprise any type of indicia representing the user, including a football helmet as depicted, a model of a generic individual, and other such indicia. The ball icon 54 preferably corresponds to the type of sports ball 11 in use. However, no claim is made as to the form or design of the player icon 53 and the ball icon 54. Furthermore, the visual representation of the tracked data may be displayed in either a two-dimensional or a three-dimensional format.

The present data visualization system may further comprise a representation of the intended route 55 of the user so that users can compare their actual route 51 to the intended route 55 so that they can determine where they need to improve in their route running. The user is preferably able to choose from a variety of routes 55 to be displayed, such as go routes, digs, and curls, using the software data visualization system of the present invention. This embodiment of the present invention is especially useful for football and other such sports, since playing these sports entails running plays that include pre-determined routes. If users are not capable of accurately running these pre-determined routes, then they will negatively impact their personal performance and the performance of their team as a whole. Therefore, receiving precise feedback on whether a route was run correctly or incorrectly is of critical importance.

The data visual representation system of the present invention further comprises the ability to time shift the visual representation of the data on the display 17, which allows users to view their route running in reverse, fast-forwarded, and in other such ways. Furthermore, the memory units of the electronic ball 11 and the user electronic tracking apparatus 15 are able to store a plurality of discrete route-running events; the present invention is adapted to show each of these events successively or is adapted to allow the user to alternate between the various discrete route-running events via the user interface. In one embodiment of the present invention, the electronic ball 11 and the user electronic tracking apparatus 15 continuously monitor, record, and store the user's activities until they are shut off. In an alternative embodiment of the present invention, the user is able to initiate recording by using a user input means, such as a button disposed on the user electronic tracking apparatus 15. In a further alternative embodiment of the present invention, the present invention is able to automatically initiate the recording of the user's and the ball's activities based upon the occurrence of a programmable variable. For example, the user may program the present invention to start recording when the user initially accelerates from a still position, record throughout the user's running of the route, and then halt recording when the user stops. This allows the present invention to record the entirety of a single route-running event without any additional unnecessary data recordation. Each of the discrete route running events is time-indexed, stored on the devices' memory units, and catalogued for future retrieval by the visual representation system of the present invention.

Figure 7A:
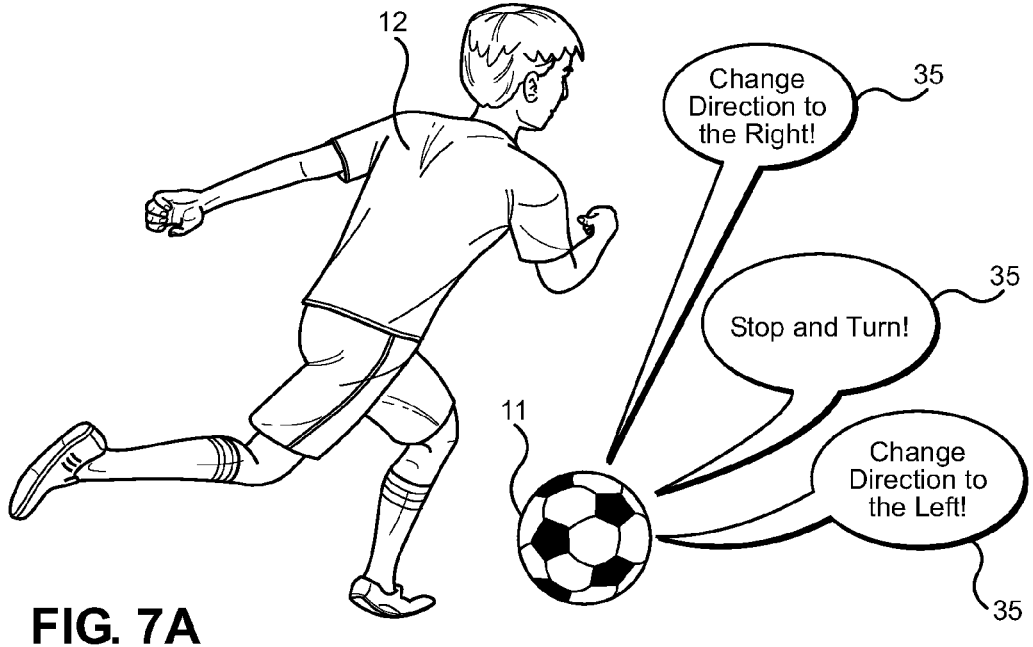
FIG. 7A shows a perspective view of an embodiment of the present invention providing direction to a user.
Figure 7B:
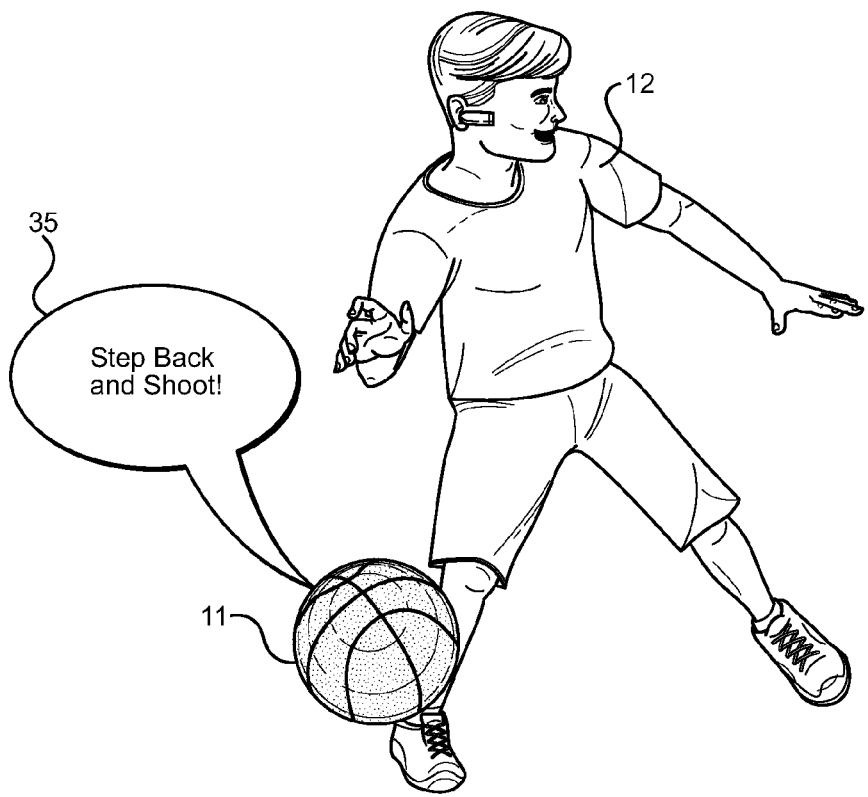
FIG. 7B shows a perspective view of an alternate embodiment of the present invention providing direction to a user.

Referring now to FIGS. 7A and 7B, there are shown perspective views of alternate embodiments of the present invention providing direction to a user. As described above, the electronic ball 11 of the present invention comprise a plurality of sensors for detecting forces, acceleration, deceleration, orientation, spin, and other such variables associated with the movement of the ball 11 or the user 12 himself or herself. The ball 11 is adapted to monitor, characterize, and store these variables and then play a noise, comment, command, or other such sound whenever the data measurement at that particular time interval falls within the tolerance range associated with one of the sounds from the pre-determined list of sounds. Each sound preferably has a pre-determined tolerance range for at least one of the variables that initiates the playing of that sound when the given variable falls within the given tolerance range, ensuring that correct comments are logically played on the occurrence of the events. The sounds may include generic noises, comments logically based upon the tracked event, and other such sounds. The present invention may be further be configured based upon the age of the user or the user's skill level. The present invention may be programmed such that certain sounds may be enabled, disabled, or have their tolerance ranges altered based upon the age or skill level of the individual. For example, the present invention may be set for a "novice" skill level and when set to this skill level, the tolerance range for initiating and playing a "Great kick!" comment may be widened to account for the fact that novice individuals are not as adept at striking a ball squarely as skilled individuals. As another example, the present invention may be set to a "child" age range, which disables all of the spoken comments or coaching commands and instead enables only noises to entertain the user. These noises may comprise rocket ship sounds, applause from a crowd, animal noises, and other such noises. The given examples are not intended to be limiting in any way, however, as the present invention may utilize any type of selectable parameter to enable or disable the programmed sounds or alter the tolerance ranges that control when the given sounds are played. However, the present invention may further comprise commands that are designed to mimic coaching direction and play at random intervals, rather than when the measured variables fall within a given tolerance range.

The present invention is adapted to mimic coaching by providing random comments 35 giving direction to the user. This coaching system may either be activated by the user or as part of a wirelessly downloadable upgrade package. The comments 35 may be either emitted through the ball's 11 speaker or transmitted to a headset via the ball's 11 wirelessly transceiver, depending upon the embodiment of the present invention. The randomized comments, which may include "Stop and turn!", "Step back and shoot!," and such, mimic coaching behavior by providing users 12 with directions that they must quickly respond and react to while using the device. This trains users 12 to follow coaching direction and also increases their agility as they are forced to respond quickly to tasks randomly assigned by the electronic subsystem housed within the ball 11. The present invention is also adapted to provide encouragement to users 12 when certain behavior is detected by the present invention's various sensors. For example, if the soccer ball embodiment of the ball 11 detects that the average force of impact exerted on the ball by the user is steadily declining over time, the ball 11 may play a "Kick harder!" comment 35. These encouragement comments 35 enable the user to improve his or her performance over time because the device automatically detects when the user's 12 effort is failing and notifies the user of such, allowing the user 12 to train harder to compensate for this increased level of fatigue. Without the present invention's ability to automatically detect the occurrence of such events over a period of time, a user may not notice when his or her effort is declining, which can lead to sloppy play and a loss of fundamentals. The comments 35 played by the ball 11 are specifically tailored for the type of ball 11 comprising the given embodiment of the present invention. This ensures that the comments are always logical and do not confuse users.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A sports tracking and coaching system, comprising:
a sports ball having a memory unit, a wireless transceiver, a speaker, and a plurality of motion sensors;
wherein said sports ball is configured to select a sound from a plurality of sounds stored in the memory unit and emit said sound in response to stimuli measured by said sensors and falling within a given tolerance range assigned to each of said sounds;
wherein said wireless transceiver is configured to upload data tracked by said motion sensors to a secondary electronic device for visualization thereon;
wherein the sports ball is configured to randomly select a plurality of voice commands from a plurality of voice commands stored in the memory unit and emit the plurality of selected voice commands from the speaker with a random time delay between each of the plurality of selected voice commands.

2. The sports tracking and coaching system of claim 1, further comprising an inner protective shell configured to protect said memory unit, said wireless transceiver, and said plurality of motion sensors.

3. The sports tracking and coaching system of claim 1, wherein said motion sensors comprise at least one accelerometer and at least one gyroscope.

4. The sports tracking and coaching system of claim 1, further comprising:
a user-worn tracking apparatus having a memory unit, a wireless transceiver, and a plurality of motion sensors;
wherein said wireless transceiver of the user-worn tracking apparatus is configured to upload data tracked by said motion sensors to the secondary electronic device for visualization thereon.

5. The sports tracking and coaching system of claim 4, wherein said user-worn tracking apparatus motion sensors comprise at least one accelerometer and at least one gyroscope.

6. The sports tracking and coaching system of claim 1, wherein said motion sensors are configured to detect the distance travelled by the ball in the air after being struck.

7. The sports tracking and coaching system of claim 1, wherein said motion sensors are configured to detect the level and direction of force imparted on the ball.

8. The sports tracking and coaching system of claim 1, wherein said motion sensors are configured to detect the changes in the orientation of the ball.

9. The sports tracking and coaching system of claim 1, wherein said motion sensors are configured to detect the rate of rotation of the ball.

10. The sports tracking and coaching system of claim 1, wherein said sounds are selectively enabled or disabled based upon a parameter input by a user.

11. A sports tracking and coaching system, comprising:
a sports ball having a memory unit, a wireless transceiver, and a plurality of motion sensors;
wherein said sports ball is configured to select a sound from a plurality of sounds stored in the memory unit and transmit said sound to a headset in response to stimuli measured by said sensors and falling within a given tolerance range assigned to each of said sounds;
wherein said wireless transceiver is configured to upload data tracked by said motion sensors to a secondary electronic device for visualization thereon;
wherein the sports ball is configured to randomly select a plurality of voice commands from a plurality of voice commands stored in the memory unit and emit the plurality of selected voice commands from the headset with a random time delay between each of the plurality of selected voice commands.

12. The sports tracking and coaching system of claim 11, further comprising an inner protective shell configured to protect said memory unit, said wireless transceiver, and said plurality of motion sensors.

13. The sports tracking and coaching system of claim 11, wherein said motion sensors comprise at least one accelerometer and at least one gyroscope.

14. The sports tracking and coaching system of claim 11, further comprising:
a user-worn tracking apparatus having a memory unit, a wireless transceiver, and a plurality of motion sensors;
wherein said wireless transceiver of the user-worn tracking apparatus is configured to upload data tracked by said motion sensors to the secondary electronic device for visualization thereon.

15. The sports tracking and coaching system of claim 14, wherein said user-worn tracking apparatus motion sensors comprise at least one accelerometer and at least one gyroscope.

16. The sports tracking and coaching system of claim 11, wherein said motion sensors are configured to detect the distance travelled by the ball in the air after being struck.

17. The sports tracking and coaching system of claim 11, wherein said motion sensors are configured to detect the level and direction of force imparted on the ball.

18. The sports tracking and coaching system of claim 11, wherein said motion sensors are configured to detect the changes in the orientation of the ball.

19. The sports tracking and coaching system of claim 11, wherein said motion sensors are configured to detect the rate of rotation of the ball.

20. The sports tracking and coaching system of claim 11, wherein said sounds are selectively enabled or disabled based upon a parameter input by a user.

* * * * *